United States Patent
Kei et al.

(10) Patent No.: US 9,766,445 B2
(45) Date of Patent: Sep. 19, 2017

(54) CELL SUCTION SUPPORT SYSTEM

(71) Applicant: YOKOGAWA ELECTRIC CORPORATION, Tokyo (JP)

(72) Inventors: Takayuki Kei, Tokyo (JP); Eiichi Goto, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 79 days.

(21) Appl. No.: 14/717,164

(22) Filed: May 20, 2015

(65) Prior Publication Data
US 2015/0362716 A1   Dec. 17, 2015

(30) Foreign Application Priority Data
Jun. 11, 2014 (JP) .................. 2014-120453

(51) Int. Cl.
| G02B 21/16 | (2006.01) |
| G01N 15/14 | (2006.01) |
| G01N 33/483 | (2006.01) |
| G02B 21/36 | (2006.01) |
| G06K 9/00 | (2006.01) |
| G01N 21/64 | (2006.01) |
(Continued)

(52) U.S. Cl.
CPC ......... G02B 21/16 (2013.01); G01N 15/1468 (2013.01); G01N 33/4833 (2013.01); G02B 21/365 (2013.01); G02B 21/368 (2013.01); G06K 9/00134 (2013.01); G06K 9/00147 (2013.01); C12M 47/06 (2013.01); G01N 15/1456 (2013.01); G01N 21/6458 (2013.01); G01N 21/6486 (2013.01); G01N 2015/1006 (2013.01); G01N 2015/149 (2013.01)

(58) Field of Classification Search
CPC .......... G01N 33/4833; G01N 15/1468; G01N 21/6458; G01N 2015/149; G01N 15/1456; G01N 21/6486; G01N 2015/1006; G02B 21/16; G02B 21/365; G02B 21/368; G06K 9/00134; G06K 9/00147; C12M 47/06
See application file for complete search history.

(56) References Cited

U.S. PATENT DOCUMENTS

| 5,106,584 A * | 4/1992 | Funakubo et al. ... G01N 35/028 422/63 |
| 7,776,584 B2 | 8/2010 | Richmond et al. |
(Continued)

FOREIGN PATENT DOCUMENTS

| JP | 2005207986 A | 8/2005 |
| JP | 2006254895 A | 9/2006 |
(Continued)

*Primary Examiner* — Gautam Prakash
(74) *Attorney, Agent, or Firm* — Sughrue Mion, PLLC

(57) ABSTRACT

A cell suction support system includes: an image acquisition unit that acquires a microscopic image of a group of cells in a cell container; an image processor that uses the microscopic image to calculate a characteristic amount of each cell, and detects a cell having a characteristic amount that satisfies a predetermined condition; a display that displays information concerning the group of cells so that the detected cell is distinguishable; and a movement controller that moves the cell container so that a designated specific cell is placed at a predetermined suction position, while moving a suction tip to the suction position.

16 Claims, 8 Drawing Sheets

(51) Int. Cl.
  *G01N 15/10*   (2006.01)
  *C12M 1/00*   (2006.01)

(56) References Cited

U.S. PATENT DOCUMENTS

| | | |
|---|---|---|
| 8,643,947 B2 | 2/2014 | Nezu et al. |
| 2006/0183215 A1 | 8/2006 | Youoku et al. |
| 2006/0194334 A1 | 8/2006 | Zhang |
| 2010/0317118 A1 | 12/2010 | Masujima et al. |
| 2011/0216404 A1 | 9/2011 | Nezu et al. |
| 2013/0027539 A1 | 1/2013 | Kiyota et al. |
| 2014/0065637 A1 | 3/2014 | Kirk et al. |
| 2014/0315237 A1 | 10/2014 | Masujima et al. |
| 2015/0198537 A1 | 7/2015 | Kimura et al. |

FOREIGN PATENT DOCUMENTS

| | | |
|---|---|---|
| JP | 2010-268723 A | 12/2010 |
| JP | 2011160726 A | 8/2011 |
| JP | 2011174791 A | 9/2011 |
| JP | 2011-229413 A | 11/2011 |
| JP | 5056871 B2 | 10/2012 |
| JP | 5157950 B2 | 3/2013 |
| JP | 5190773 B2 | 4/2013 |
| JP | 5317983 B2 | 10/2013 |
| JP | 2014-039520 A | 3/2014 |
| WO | 2009/063776 A1 | 5/2009 |
| WO | 2011089908 A1 | 7/2011 |
| WO | 2014/057713 A1 | 4/2014 |

\* cited by examiner

FIG. 3A
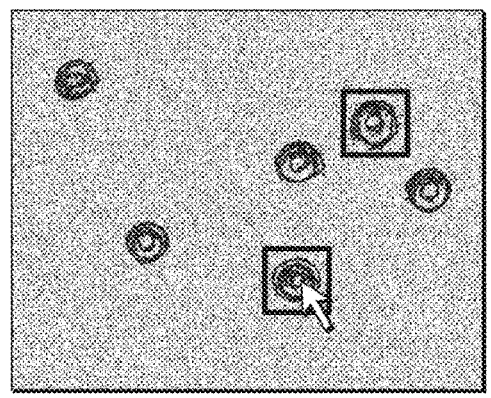
FIG. 3B
| IDENTIFIER | POSITION | SIZE | BRIGHTNESS #1 | BRIGHTNESS #2 | ... |
|---|---|---|---|---|---|
| aaa | xaa yaa | a111 | a112 | a113 | ... |
| bbb | xbb ybb | b111 | b112 | b113 | ... |
| ccc | xcc ycc | c111 | c112 | c113 | ... |
| ddd | xdd ydd | d111 | d112 | d113 | ... |
| eee | xee yee | e111 | e112 | e113 | ... |
| ⋮ | ⋮ | ⋮ | ⋮ | ⋮ | |
FIG. 3C
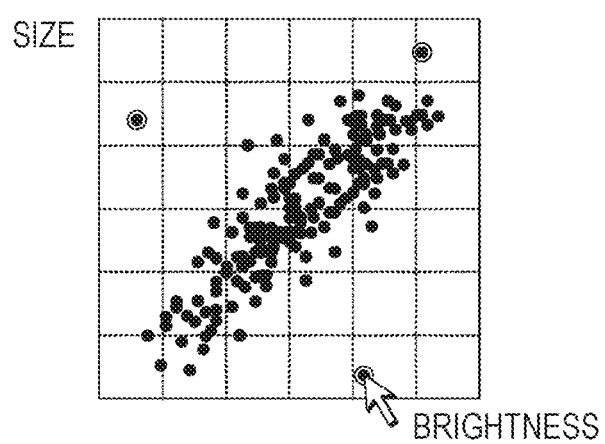

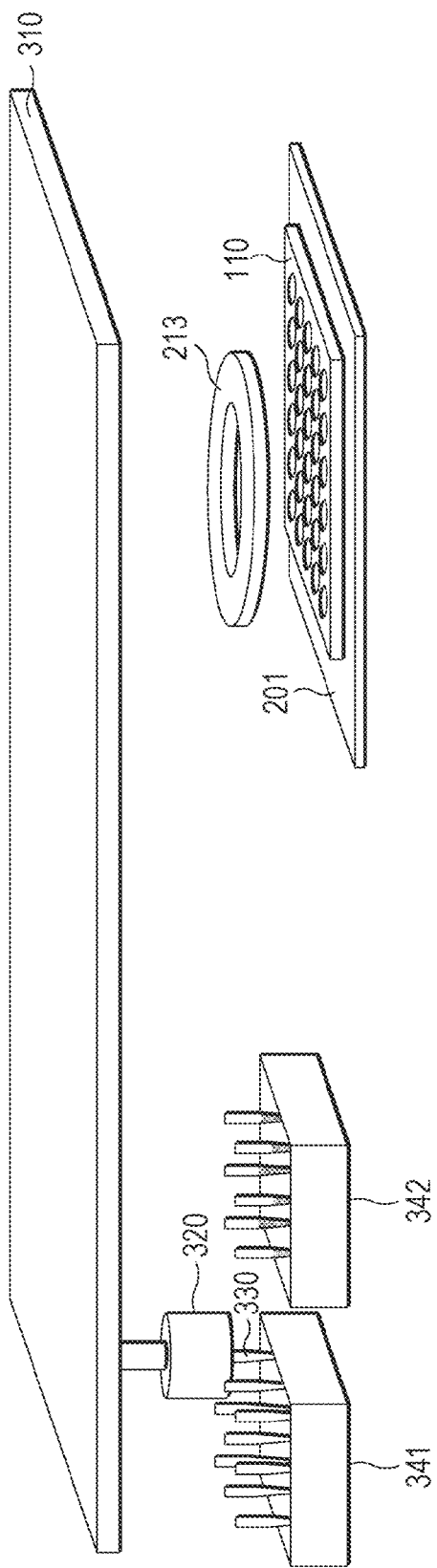

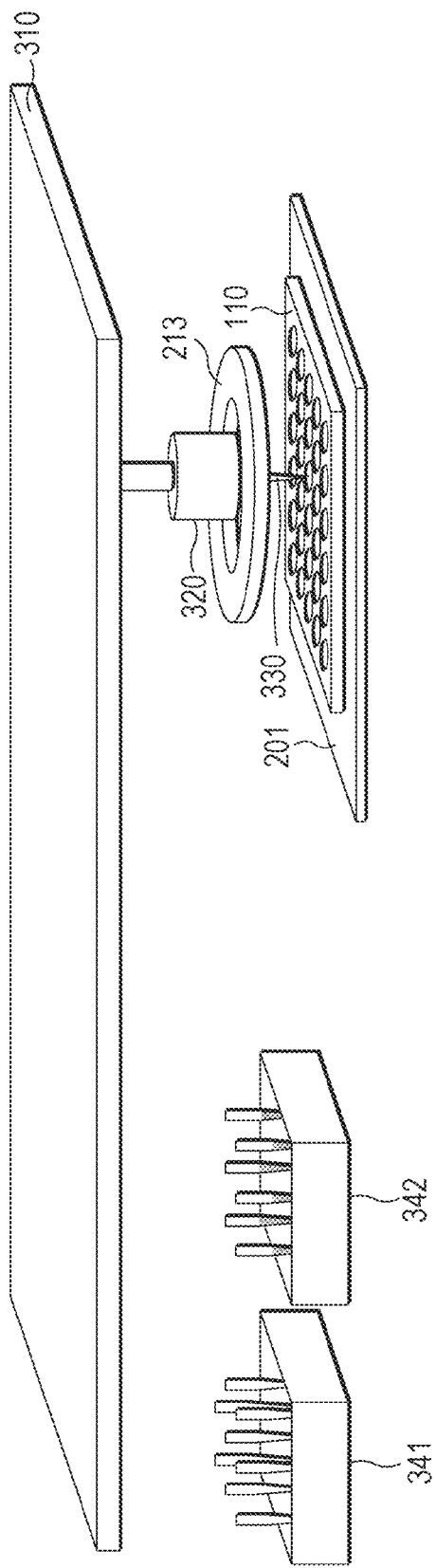

330

CELL SUCTION SUPPORT SYSTEM

CROSS-REFERENCE TO RELATED APPLICATION

This application claims priority from Japanese Patent Application No. 2014-120453 filed with the Japan Patent Office on Jun. 11, 2014, the entire content of which is hereby incorporated by reference.

BACKGROUND

1. Technical Field

The present disclosure relates to a cell suction support system that supports an operation of sucking cells or cell components.

2. Description of the Related Art

In studies of the biological system, there are frequently performed operations of identifying a characteristic cell among plenty of cells in a cell culture well, and of sucking the identified cell or a component of the cell. For example, a drug development screening process is performed during a course of drug development for finding or designing a new drug. In this process, a compound indicating drug efficacy and/or activity is searched among plenty of candidate compounds. During this process, a cell indicating a significantly unique change is selected from a group of cells in a cell culture well in which a candidate compound is provided. Furthermore, the selected cell or a cell component of the cell is sucked, and analysis such as mass spectrometry is performed to the sucked cell or cell component.

In the operation of sucking a cell, an operator performs the operation using a dispenser and a suction pipette equipped with a suction tip while identifying a cell to be sucked through a microscope. In the operation of sucking a cell component, an operator performs the operation using a microscopic tip called a nanospray tip while identifying a cell to be sucked through a microscope.

Furthermore, apart from the operation of sucking and analyzing a specific cell or cell component in a cell culture well, a cell analysis system that performs the following operations has been practically used. That is, this system photographs a microscopic image of a large volume of cells in a cell culture well, and performs image processing of the photographed image. Accordingly, this system distinguishes individual cells, and calculates in real time a characteristic amount, such as size or brightness, of each cell.

In the above-described cell analysis system, an operator can detect a characteristic cell and observe a time-dependent change of the cell, based on the calculated characteristic amount. Furthermore, the characteristic amount of each cell is illustrated in a histogram or a scatter diagram, and is also displayed in a list. However, this cell analysis system only performs analysis with the characteristic amount obtained from the image. This cell analysis system is not assumed to analyze in detail a specific cell that has been found by the analysis.

It is noted that literatures related to this art include, for example, Japanese Patent No. 5317983, Japanese Patent No. 5190773, Japanese Patent No. 5056871 and Japanese Patent No. 5157950.

SUMMARY

A cell suction support system includes: an image acquisition unit that acquires a microscopic image of a group of cells in a cell container; an image processor that uses the microscopic image to calculate a characteristic amount of each cell, and detects a cell having a characteristic amount that satisfies a predetermined condition; a display that displays information concerning the group of cells so that the detected cell is distinguishable; and a movement controller that moves the cell container so that a designated specific cell is placed at a predetermined suction position, while moving a suction tip to the suction position.

BRIEF DESCRIPTION OF DRAWINGS

FIGS. 3A to 3C are diagrams illustrating a display example of analysis results;

FIG. 4 is a diagram illustrating a movement of a suction unit before cell suction;

FIG. 5 is a diagram illustrating a movement of a suction unit and a microplate during cell suction;

DESCRIPTION OF THE EMBODIMENTS

Figure 1:
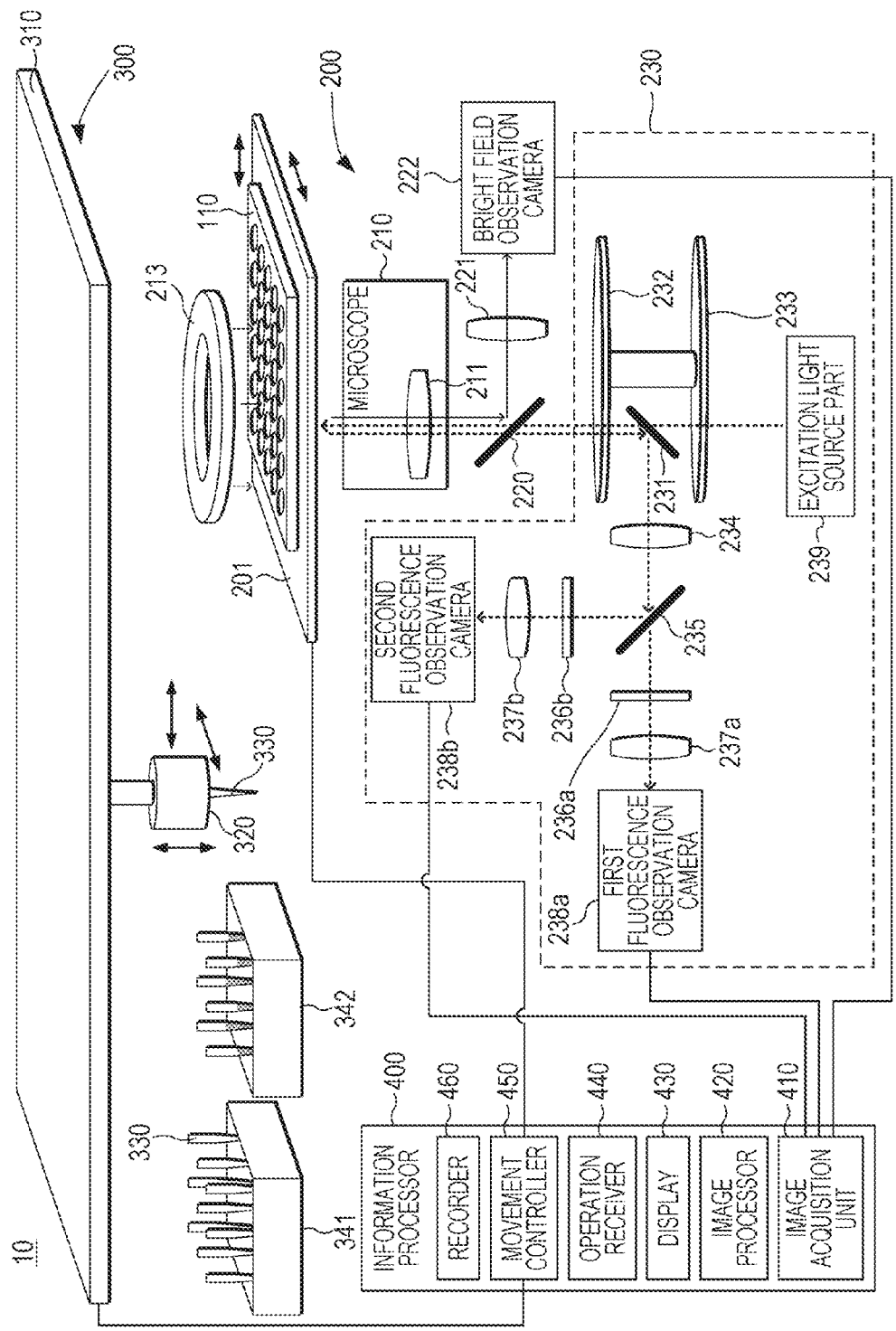
FIG. 1 is a diagram illustrating a configuration of a cell suction support system according to the present embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In the operation of sucking a cell or a cell component, an operator selects a cell to be analyzed while visually inspecting individual cells. For this reason, the handling of a large volume of cells took much time and labor, causing a burden of an operator to become heavier. Therefore, it is desired to develop a system that can simply detect a candidate cell to be analyzed among a large volume of cells, and that can immediately suck the detected cell.

An object of the present disclosure is to provide a system that supports a suction operation of a characteristic cell among a large volume of cells.

A cell suction support system (this system) according to an embodiment of the present disclosure includes: an image acquisition unit that acquires a microscopic image of a group of cells in a cell container; an image processor that uses the microscopic image to calculate a characteristic amount of each cell, and detects a cell having a characteristic amount that satisfies a predetermined condition; a display that displays information concerning the group of cells so that the detected cell is distinguishable; and a movement controller that moves the cell container so that a designated specific cell is placed at a predetermined suction position, while moving a suction tip to the suction position.

This system may further include an operation receiver that receives designation of the specific cell.

This system may further include bright field illumination that illuminates the cell container and is provided with a space in a center of the illumination.

This system may further include a fluorescence observation camera that photographs the group of cells in the cell container to obtain a fluorescence observation image as the microscopic image. A leading end of the suction tip may be coated with a fluorescence substance.

This system may further include a fluorescence observation camera that photographs the group of cells in the cell container to obtain a fluorescence observation image as the microscopic image. The suction tip may be irradiated with light having a wavelength that is visually recognizable by the fluorescence observation camera.

The characteristic amount can include at least one of cell size and cell brightness.

The image acquisition unit may further acquire microscopic images of the group of cells in the cell container before and after a cell is sucked by the suction tip.

This system may further include a recorder for recording the microscopic images of the group of cells in the cell container before and after a cell is sucked by the suction tip, while associating the microscopic images with the tip having sucked the cell.

This system can support a suction operation of a characteristic cell among a large volume of cells.

An embodiment of the present disclosure will be described with reference to the drawings. FIG. 1 is a diagram illustrating a configuration of a cell suction support system 10 according to the present embodiment. The cell suction support system 10 is an apparatus that supports a suction process of a cell or a cell component. The cell suction support system 10 includes an optical system part 200, a suction action part 300, and an information processor 400. Hereinafter, unless otherwise distinguished, the suction of a cell includes not only the suction of one cell but also the suction of a cell component such as an intracellular organelle. That is, hereinafter, an expression "cell" means not only a cell but also a cell component in some cases.

The optical system part 200 includes: an XY stage 201 on which a microplate (a cell culture container or a cell container) 110, having a plurality of wells formed thereon, is to be placed; a microscope 210 containing an objective lens 211; bright field illumination 213; a dichroic mirror 220; a variable magnification lens 221; a bright field observation camera 222; and a confocal scanner part 230.

It is noted that, other than the microplate 110, an optional cell culture container (cell container), such as a cell culture dish, a cover glass chamber, and a petri dish, can be placed on the XY stage 201.

Also, in the present embodiment, there will be described, as an example, the optical system part 200 configured to include: a focal point optical system that performs fluorescence observation with two-color light; and an optical system that performs bright field observation. However, the optical system part 200 is not limited to this configuration. For example, the optical system part 200 may not include a confocal scanner part 230 and the bright field observation system. That is, the optical system part 200 may be configured to include one-color epifluorescence. Furthermore, the optical system part 200 may be a confocal optical system that performs one-color fluorescence observation. Furthermore, the optical system part 200 may be configured to include a confocal optical system that performs one-color fluorescence observation and an optical system that performs bright field observation.

The confocal scanner part 230 includes a dichroic mirror 231, a pinhole array disk (Nipkow disk) 232, a microlens array disk 233, a relay lens 234, a dichroic mirror 235, a first bandpass filter 236a, a first lens 237a, a first fluorescence observation camera 238a, a second bandpass filter 236b, a second lens 237b, a second fluorescence observation camera 238b, and an excitation light source part 239.

In the bright field observation, light is emitted from the bright field illumination 213 toward the microplate 110. That is, the bright field illumination 213 irradiates the microplate 110. A bright field signal light from the microplate 110 passes through the microscope 210, is reflected on the dichroic mirror 220, and forms an image on the bright field observation camera 222 through the variable magnification lens 221. It is noted that a space is formed in a center portion of the bright field illumination 213. The bright field illumination 213 has a shape of, for example, a circular ring (doughnut).

In the fluorescence observation, a luminous flux of excitation light having a particular wavelength (an excitation light flux) is injected from the excitation light source part 239 toward the microplate 110. A sample excited by the excitation light flux emits fluorescence signals having a wavelength longer than that of the excitation light flux. The fluorescence signals having passed through the pinhole array disk 232 forms a confocal image. The fluorescence signals are reflected on the dichroic mirror 231, and form images on the first fluorescence observation camera 238a and the second fluorescence observation camera 238b through the relay lens 234. The first fluorescence observation camera 238a and the second fluorescence observation camera 238b are each a fluorescence observation camera that photographs a region (a region containing a group of cells) in the microplate 110 to obtain a fluorescence observation image as a microscopic image.

To deal with simultaneous use of the excitation light source having a plurality of wavelengths, there is disposed the dichroic mirror 235 having a property of dispersing fluorescence signals. Furthermore, in order to increase S/N ratios of images, and allow only fluorescence signals having wavelengths within a necessary wavelength band to pass through, the first bandpass filter 236a and the second bandpass filter 236b are disposed. Fluorescence signals having various fluorescence wavelengths are emitted from a sample. For example, filter wheels or the like are desirably used to prepare (dispose) a plurality of bandpass filters 236 that correspond to necessary wavelengths.

The suction action part 300 includes an XYZ stage 310, a suction unit 320, a tip rack 341, and a specimen rack 342. The tip rack 341 houses a plurality of tips 330 for sucking cells or cell components. The specimen rack 342 stores the tips 330 having sucked cells or cell components.

The suction unit 320 moves in X-axis, Y-axis and Z-axis directions with the XYZ stage. During the operation of sucking a cell, the suction unit 320 acquires one of the tips 330 from the tip rack 341 and carries the acquired tip 330. Then, the suction unit 320 moves in a direction of the microplate 110, and sucks a cell from a well at a predetermined suction position. The suction position may be, for example, on the optical axis of the microscope 210.

At this time, the XY stage 201 moves the microplate 110 so that a cell to be sucked is positioned at the suction position. Accordingly, the tip 330 and the cell to be sucked vertically overlap each other. It is noted that the bright field illumination 213 has a shape of a circular ring, in order to inhibit the bright field illumination 213 and the suction unit 320 from interfering with each other during the suction operation.

After a cell has been sucked, the suction unit 320 moves in a direction of the specimen rack 342, and releases the tip 330 having sucked a cell into the specimen rack 342 for storing.

The information processor 400 can be configured by an information processing apparatus such as a PC. The information processor 400 includes an image acquisition unit 410, an image processor 420, a display 430, an operation receiver 440, a movement controller 450, and a recorder 460.

The image acquisition unit 410 drives (controls) the bright field observation camera 222, the first fluorescence observation camera 238a, and the second fluorescence observation camera 238b to photograph a region (a region containing a group of cells) in the microplate 110, thereby acquiring images (microscopic images) of a group of cells in the microplate 110.

The image processor 420 uses the images acquired by the image acquisition unit 410 to calculate a characteristic amount of each cell, and detects a cell having a characteristic amount that satisfies a predetermined condition. For example, the image processor 420 performs image processing for the images acquired by the image acquisition unit 410. Furthermore, the image processor 420 uses results of the image processing to perform various analyses. Specifically, the image processor 420 recognizes (distinguishes) cells (including organelles (cell components)) by template matching or the like. Furthermore, the image processor 420 calculates a characteristic amount such as size, brightness, protein amount, and/or ion amount for each of the distinguished cells. The image processor 420 also uses the calculated characteristic amounts to generate a list or a graph concerning information related to the cell.

The display 430 displays information concerning a group of cells so that the cell detected by the image processor 420 is distinguishable. That is, the display 430 displays, for example, the images acquired by the image acquisition unit 410 and/or the analysis results of the image processor 420.

The operation receiver 440 receives various operations from an operator. For example, the operation receiver 440 receives designation of a specific cell from an operator.

The movement controller 450, for example, moves the microplate 110 so that the specific cell designated by an operator is placed at a predetermined suction position, while moving the suction tip 330 to the suction position. The movement controller 450 controls movements of the XY stage 201 and the XYZ stage 310 to move the microplate 110 and the suction unit 320.

The recorder 460 records, for example, the images acquired by the image acquisition unit 410 and/or the analysis results of the image processor 420.

Next, the actions of the cell suction support system 10 will be described with reference to the flowchart in FIG. 2. It is noted that the actions described below is an example. The cell suction support system 10 can perform an operation of sucking a cell in various procedures depending on the analysis plan of an operator.

First, the cell suction support system 10 receives setting of a sample to be used for analysis or the like from an operator (S101). That is, an operator sets the microplate 110 in which cells are cultivated (the microplate 110 on which a group of cells is placed), at a predetermined position in the cell suction support system 10. At that time, an operator performs fluorescence staining as necessary. Also, an operator places the tips 330 corresponding to the purpose of suction on the tip rack 341. For example, an operator places nanospray tips when performing suction of cell components, and common suction tips when performing suction of one cell.

Subsequently, the operation receiver 440 receives a photographing condition or the like (S102) while receiving an analysis content or the like (S103). In the receipt of a photographing condition, for example, optical system conditions, such as confocal, epifluorescence, and phase differences, are designated; wavelengths are set; and/or photographing intervals, total photographing times, and the like are set. The designation of confocal facilitates three-dimensional component selection during the suction of a cell.

In the receipt of an analysis content, a calculation object of a characteristic amount, and/or a detection condition of a remarked cell are set. The characteristic amount includes, for example, the brightness and size of a cell. In the setting of a detection condition, a threshold value of the characteristic amount and the like are set. The setting of a detection condition allows for automatic detection of a cell satisfying the detection condition.

Then, the operation receiver 440 receives the setting of a photographing range (S104). Thereafter, the image acquisition unit 410 drives the bright field observation camera 222, the first fluorescence observation camera 238a, and the second fluorescence observation camera 238b to photograph a region (a region containing a group of cells) in the microplate 110 (S105). The image acquisition unit 410 may use some of these cameras.

This photographing allows the image acquisition unit 410 to acquire images (for example, microscopic images) of a group of cells in the microplate 110. The image processor 420 performs analysis by image processing of the acquired images (S106). In the analysis by image processing, the image processor 420 detects a cell satisfying an extraction condition (a predetermined condition). Then, the display 430 displays analysis results (S107). In the display of analysis results, the display 430 displays information concerning a group of cells, in such a manner that the cell satisfying the detection condition is apparent (that is, in such a manner that the cell detected by the image processor 420 (the cell satisfying the extraction condition) is distinguishable).

Specifically, in the display of analysis results, for example, as the information concerning a group of cells, the cells satisfying the detection condition may be clearly indicated in the microscopic image as illustrated in FIG. 3A. Alternatively, as illustrated in FIG. 3B, the recognized cells may be listed, and the cells satisfying the detection condition may be highlighted. Alternatively, as illustrated in FIG. 3C, a scatter diagram may be displayed based on the characteristic amounts of the recognized cells. In an example of FIG. 3C, the scatter diagram has axes of size and brightness of cells, and the cells satisfying the detection condition are remarked. The display of analysis results (for example, information concerning a group of cells) is not limited to these examples, and can be in a variety of forms.

An operator can designate a specific cell as an object to be sucked according to the analysis results. In the designation of an object to be sucked, an optional cell may be designated, or the detected cells may be automatically designated one by one.

When an operator designates an optional cell, for example, an operator may merely click a cell to be sucked on the microscopic image illustrated in FIGS. 3A to 3C. The image processor 420 distinguishes individual cells. For this reason, the designation of a specific cell in a display image enables the image processor 420 to identify the designated cell in the microplate 110.

Figure 2:
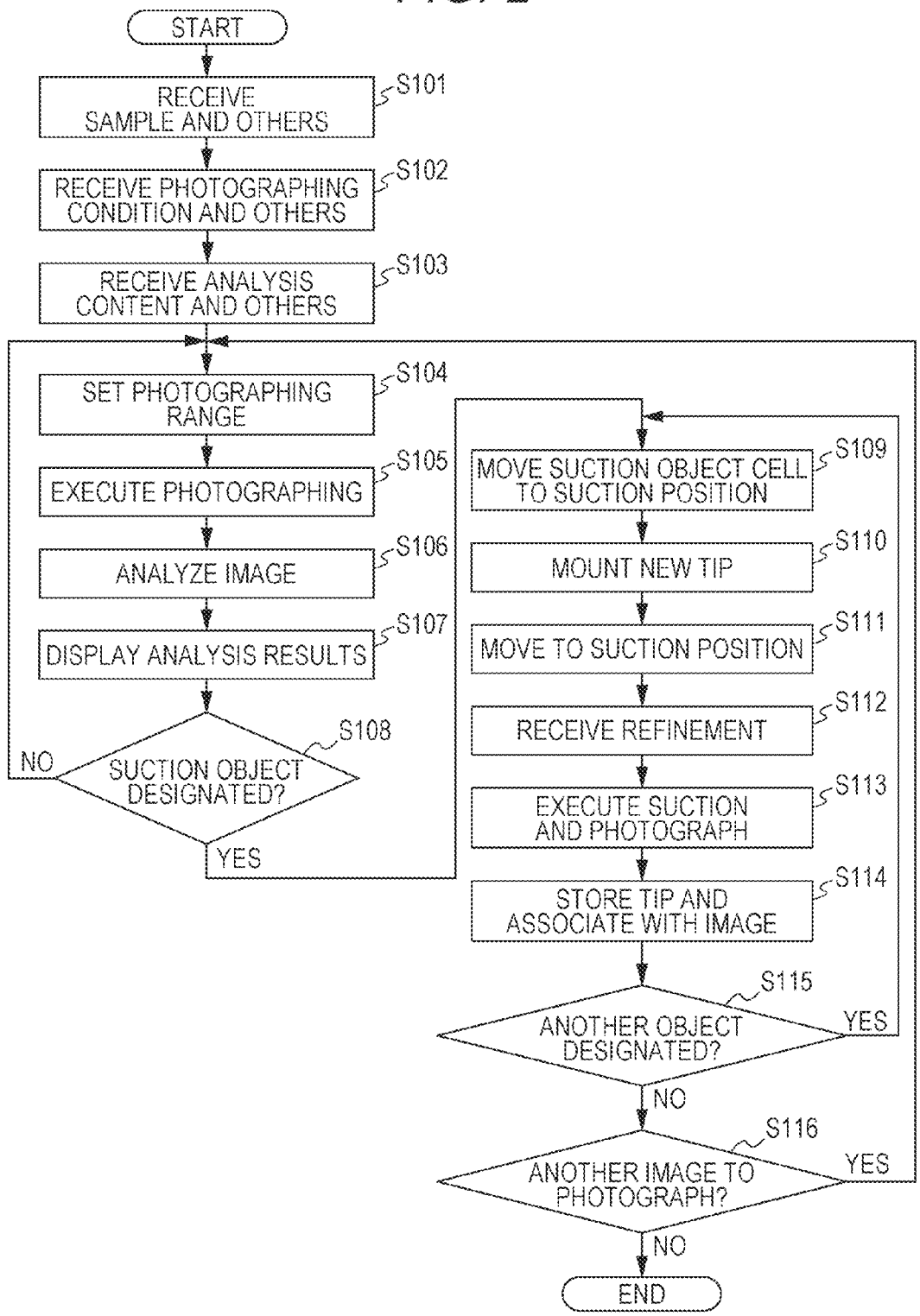
FIG. 2 is a flowchart explaining actions of the cell suction support system.

Returning to the description of the flowchart of FIG. 2, when a cell to be sucked is not designated (S108: No), a photographing range is reset (S104), and the following processes (S105 to S107) are repeated.

When a cell to be sucked is designated (S108: Yes), the movement controller 450 controls the XY stage 201 to move the designated cell to be sucked to a suction position (S109). The suction position is, for example, on the optical axis of the microscope 210.

The movement controller 450 also controls the XYZ stage 310 to move the suction unit 320 in a direction of the tip rack 341 as illustrated in FIG. 4. Furthermore, the movement controller 450 mounts a new tip 330 to the suction unit 320(S110).

Then, the movement controller 450 controls the XYZ stage 310 to move the suction unit 320 so that the tip 330 overlaps or substantially overlaps the suction position as illustrated in FIG. 5 (S111). Since a space is provided in the center of the bright field illumination 213, the bright field illumination 213 and the suction unit 320 can be inhibited from interfering with each other at this time.

As a result of the process (S110) and the process (S111), the cell to be sucked and the tip 330 vertically overlap each other at the suction position. For this reason, the cell to be sucked can be easily sucked. However, when the cell is sucked, the cell has sometimes moved from the position when the image was acquired. In addition, an object to be sucked is sometimes a specific organ (a cell component) in a cell. To address this concern, the operation receiver 440 may receive refinement of the position of the suction unit 320 or the microplate 110 from an operator (S112). In such a case, the operation receiver 440 may be configured to also receive adjustment of the suction unit 320 in a Z-axis direction.

Figure 6:
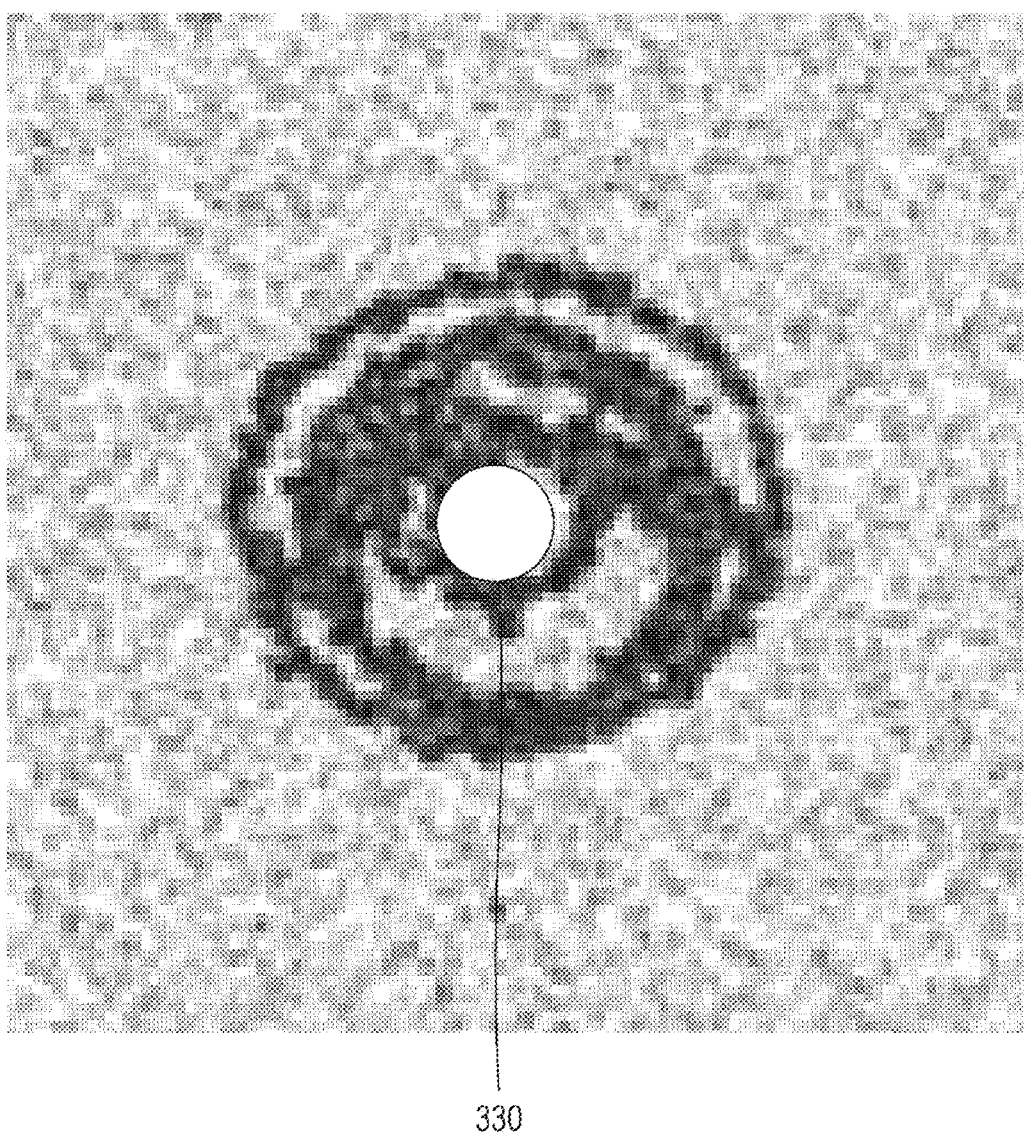
FIG. 6 is a diagram explaining refinement of a tip position during cell suction.

In the refinement of a position, the display 430 can display a microscopic image in real time as illustrated in FIG. 6. Furthermore, the operation receiver 440 may receive a movement instruction from an operator. In such a case, a leading end of the tip 330 is desirably coated with a fluorescence substance so that the position of the tip 330 can also be recognized based on a fluorescence observation image. Alternatively, LED light source (fluorescence light source) may be disposed in the vicinity of the tip attached to the suction unit 320, and predetermined-wavelength light may be emitted on the tip 330 (the leading end direction of the tip 330) to visualize the tip 330. This LED light source (fluorescence light source) emits, onto the suction tip 330, for example, light having a wavelength that can be visually recognized by the first fluorescence observation camera 238a and the second fluorescence observation camera 238b.

After the refinement of a position is completed, the suction of a cell is executed (S113). At this time, the image acquisition unit 410 photographs images (for example, microscopic images) of a region (a region containing a group of cells) in the microplate 110 before and after the suction of a cell. This allows an operator to also check the certainty of the suction operation in an ex-post manner.

Figure 7:
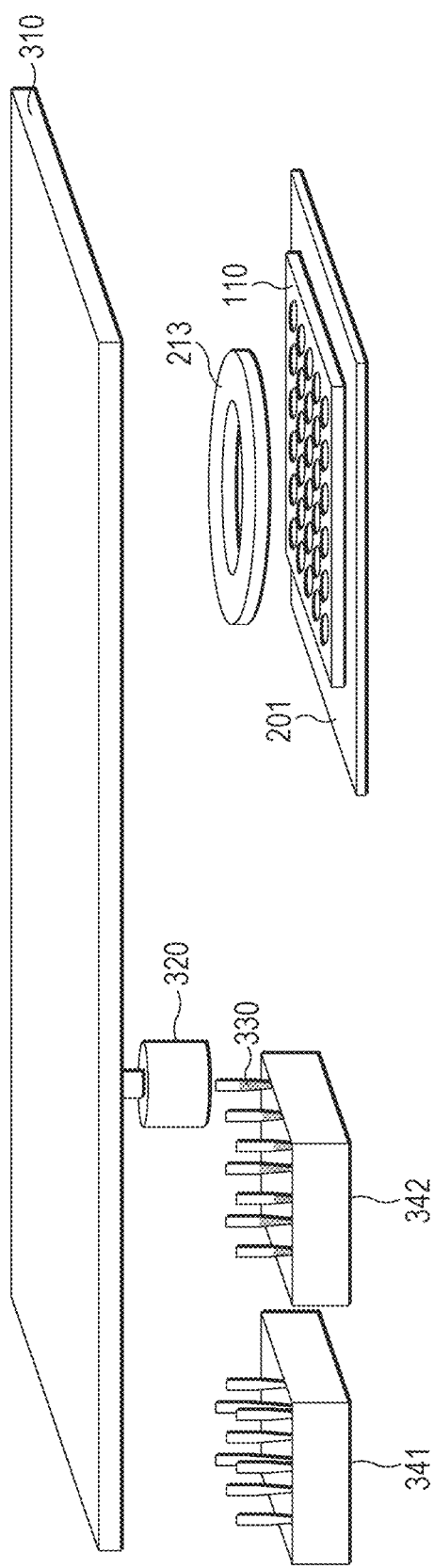
FIG. 7 is a diagram illustrating a movement of a suction unit after cell suction.

After the suction of a cell is completed, the movement controller 450 controls the XYZ stage 310 to move the suction unit 320 in a direction of the specimen rack 342 as illustrated in FIG. 7, and releases the tip 330 having sucked a cell into the specimen rack 342 to store the released tip 330 (S114). Also, the recorder 460 records the images photographed during the suction operation while associating the images with the tip 330 having sucked the cell. That is, the recorder 460 records the microscopic images of a group of cells in the microplate 110 before and after the cell is sucked by the suction tip 330, while associating the microscopic images with the tip 330 having sucked the cell.

When there is a suction instruction for another cell in the image photographed in the process (S105) (S115: Yes), the process of moving the cell to the suction position (S109) and the following processes (S110 to S114) are repeated.

When there is no suction instruction for another cell in the image photographed in the process (S105) (S115: No), the operation receiver 440 photographs further another image to check if the suction operation is to be continued. When the operations of photographing another image and sucking a cell are continued (S116: Yes), the process (S104) of defining a photographing range and subsequent processes are repeated. When another image is not to be photographed (S116: No), the suction operation terminates.

As described above, a series of actions performed in the cell suction support system 10 according to the present embodiment includes: photographing a region containing a group of cells; detecting a characteristic cell by image processing; and moving a cell to be sucked to a suction position. This significantly reduces an operation load of an operator engaged in the suction operation of a characteristic cell among a large volume of cells.

In the suction operation by the cell suction support system 10, one cell can be sucked. Furthermore, by using a nano-spray tip as the tip 330, a specific cell component can also be sucked. In this case, highly sensitive mass spectrometry can be performed. Furthermore, when one cell is an object to be sucked, the selection of a specific cell enables delamination, selection, and removal of the cell from a large volume of cells. Therefore, the cell suction support system 10 may also be expected to be applied in the regenerative medicine field or the like.

Figure 8A:
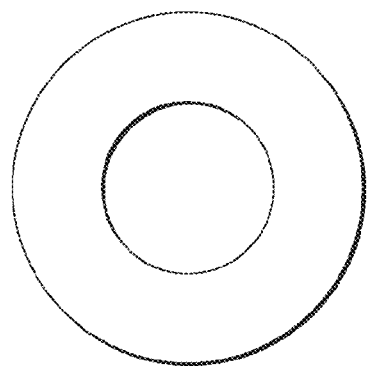
FIGS. 8A to 8D are diagrams explaining a shape example of bright field illumination.
Figure 8B:
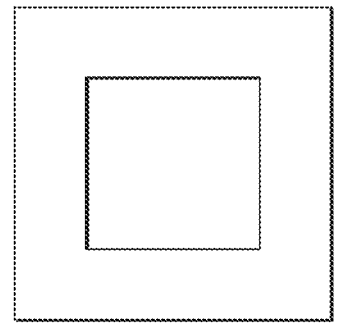
Figure 8C:
Figure 8D:
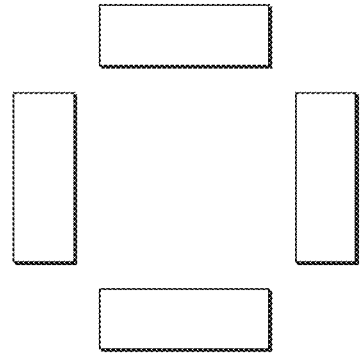

It is noted that, as described above, a space is provided in the center of the bright field illumination 213, in order to inhibit the bright field illumination 213 and the suction unit 320 from interfering with each other while a cell is sucked. The bright field illumination 213 does not necessarily have a shape of a circular ring (a doughnut) as illustrated in FIG. 8A, as long as it has a space in the center portion. The bright field illumination 213 may have a shape of, for example, a rectangular frame as illustrated in FIG. 8B. Furthermore, as illustrated in FIGS. 8C and 8D, the bright field illumination 213 may have a shape of being divided into a plurality of portions.

It is noted that in the present embodiment, the image acquisition unit 410 drives (controls) the bright field observation camera 222, the first fluorescence observation camera 238a, and the second fluorescence observation camera 238b to photograph a region (a region containing a group of cells) in the microplate 110. However, instead of this, another member that drives (controls) the bright field observation camera 222, the first fluorescence observation camera 238a, and the second fluorescence observation camera 238b to photograph a group of cells may be disposed in the information processor 400. Alternatively, the information processor 400 may photograph the region.

An embodiment according to the present disclosure may be a cell suction support system that supports a suction operation of a cell or a cell component. Furthermore, an embodiment according to the present disclosure may be a cell suction support system that is suitable for a suction operation of a large volume of cells.

Also, in the present embodiment, the optical system part 200 may be configured to perform two-color confocal fluorescence observation and bright field observation. However, the optical system part 200 is not limited to this configuration. For example, the optical system part 200 may have a configuration of one-color epifluorescence without the confocal scanner part 230 and the bright field observation system, a configuration of one-color confocal, or a configuration of one-color confocal and bright field.

The cell suction support system according to an embodiment of the present disclosure may be the following first to fifth cell suction support systems.

The first cell suction support system is a cell suction support system that supports an operation of sucking a specific cell or cell component from a group of cells in a cell culture container, and includes: an image acquisition unit that acquires a microscopic image of the group of cells; an image processor that distinguishes individual cells based on the acquired image to calculate a characteristic amount for each cell, and detects a cell that has a characteristic amount satisfying a predetermined condition; a display that displays information concerning the group of cells in such a manner that the detected cell is distinguishable; and an action control unit that, when receiving designation of a specific cell in the information concerning a group of cells, moves the cell culture container so that the specific cell is located at a predetermined suction position, while moving a suction tip to the suction position.

The second cell suction support system according to the first cell suction support system further includes bright field illumination for illuminating the cell culture container. A space is disposed in a center of the bright field illumination.

In the third cell suction support system according to the first or second cell suction support system, the image is a fluorescence observation image, and a leading end of the suction tip is coated with a fluorescence substance, or irradiated with light having a wavelength that can be visually recognized in the fluorescence observation image.

In the fourth cell suction support system according to any one of the first to third cell suction support systems, the characteristic amount includes one of cell size and cell brightness.

In the fifth cell suction support system according to any one of the first to fourth cell suction support systems, the image acquisition unit further acquires microscopic images before and after a cell is sucked by the suction tip.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A cell suction support system comprising:
   at least one light source configured to illuminate a cell container comprising at least one cell well, the at least one light source comprises at least one of at least one fluorescence illumination, and at least one bright field illumination;
   at least one camera operative to acquire at least one image of the at least one cell well illuminated by said at least one light source;
   at least one information processor configured to execute:
      image acquisition to operate said at least one camera to acquire the at least one image of the at least one cell well;
      image processing to:
         match at least one part of the at least one acquired image with at least one template image, and
         detect and identify, based on a result of the match, a specific cell in the at least one cell well having a characteristic amount of at least one parameter that satisfies a predetermined condition; and
      movement control to control at least one of movement of the cell container so that the specific cell is placed at a predetermined suction position, and movement of a suction tip to the predetermined suction position;
   a display configured to display information concerning the at least one cell well so that the specific cell is distinguishable;
   a first stage configured to move, in response to the movement control, the cell container so that the specific cell is placed at the predetermined suction position; and
   a second stage configured to move, in response to the movement control, the suction tip to the predetermined suction position to perform suction of the cell such that the suction tip is disposed perpendicularly to the predetermined suction position, wherein
   when the at least one light source includes the at least one bright field illumination, the suction tip suctions the specific cell through a space provided in a center of the bright field illumination.

2. The cell suction support system according to claim 1, wherein
   the specific cell or a specific organ in the cell are suctioned by the suction tip.

3. The cell suction support system according to claim 1, wherein the said at least one information processor is further configured to execute:
   a receiving operation to receive designation of the specific cell.

4. The cell suction support system according to claim 3, wherein
   the specific cell or a specific organ in the cell are suctioned by the suction tip.

5. The cell suction support system according to claim 1, wherein the at least one camera includes a fluorescence observation camera configured to photograph the at least one cell well in the cell container to obtain a fluorescence observation image as the at least one image, wherein a leading end of the suction tip is coated with a fluorescence substance.

6. The cell suction support system according to claim 1, wherein the at least one camera includes a fluorescence observation camera configured to photograph the at least one cell well in the cell container to obtain a fluorescence observation image as the at least one image,
   wherein the suction tip is irradiated with light having a wavelength that is visually recognizable by the fluorescence observation camera.

7. The cell suction support system according claim 1, wherein the characteristic amount includes at least one of cell size and cell brightness.

8. The cell suction support system according to claim 1, wherein the said at least one information processor is further configured to execute:
   the image acquisition to further operate said at least one camera to acquire at least one image of the at least one cell well in the cell container before and after the specific cell is suctioned by the suction tip.

9. The cell suction support system according to claim 8, wherein the said at least one information processor is further configured to execute:
 a recording operation to record the at least one image of the at least one cell well in the cell container before and after the specific cell is suctioned by the suction tip, while associating the at least one image with the tip having suctioned the cell.

10. The cell suction support system according to claim 1, wherein the at least one light source comprises a source of bright field light.

11. The cell suction support system according to claim 1, wherein the at least one light source comprises a source of fluorescence light.

12. The cell suction support system according to claim 1, wherein the at least one camera comprises at least one of a fluorescence observation camera and a bright field observation camera.

13. The cell suction support system according to claim 1, further comprising a confocal scanner configured to obtain the at least one image by photographing the at least one cell well.

14. The cell suction support system according to claim 1, wherein suction of the cell includes at least one of suction of one cell and suction of a cell component.

15. A cell suction support system comprising:
 at least one light source configured to illuminate a cell container comprising at least one cell well;
 at least one camera operative to acquire at least one image of the at least one cell well illuminated by said at least one light source;
 at least one information processor configured to execute:
  image acquisition to operate said at least one camera to acquire the at least one image of the at least one cell well;
  image processing to:
   match at least one part of the at least one acquired image with at least one template image, and
   detect and identify, based on a result of the match, a specific cell in the at least one cell well having a characteristic amount of at least one parameter that satisfies a predetermined condition; and
  movement control to control at least one of movement of the cell container so that the specific cell is placed at a predetermined suction position, and movement of a suction tip to the predetermined suction position;
 a display configured to display information concerning the at least one cell well so that the specific cell is distinguishable;
 a first stage configured to move, in response to the movement control, the cell container so that the specific cell is placed at the predetermined suction position; and
 a second stage configured to move, in response to the movement control, the suction tip to the predetermined suction position to perform suction of the cell, wherein the movement control causes the at least one processor to adjust a position of the suction tip such that the suction tip is positioned perpendicularly to the predetermined suction position.

16. The cell suction support system according to claim 15, wherein the specific cell or a specific organ in the cell are suctioned by the suction tip.

\* \* \* \* \*